(12) United States Patent
Matsunaga

(10) Patent No.: US 10,586,331 B2
(45) Date of Patent: Mar. 10, 2020

(54) DIAGNOSIS ASSISTING DEVICE, IMAGE PROCESSING METHOD IN DIAGNOSIS ASSISTING DEVICE, AND NON-TRANSITORY STORAGE MEDIUM HAVING STORED THEREIN PROGRAM

(71) Applicant: CASIO COMPUTER CO., LTD., Shibuya-ku, Tokyo (JP)

(72) Inventor: Kazuhisa Matsunaga, Fussa (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 251 days.

(21) Appl. No.: 15/642,275

(22) Filed: Jul. 5, 2017

(65) Prior Publication Data

US 2018/0061051 A1  Mar. 1, 2018

(30) Foreign Application Priority Data

Sep. 1, 2016 (JP) .................................. 2016-170477
Apr. 17, 2017 (JP) .................................. 2017-081415

(51) Int. Cl.
*G06K 9/00* (2006.01)
*G06T 7/00* (2017.01)
(Continued)

(52) U.S. Cl.
CPC ............ *G06T 7/0014* (2013.01); *A61B 5/444* (2013.01); *A61B 5/7267* (2013.01); *G06K 9/46* (2013.01);
(Continued)

(58) Field of Classification Search
None
See application file for complete search history.

(56) References Cited

U.S. PATENT DOCUMENTS 5,465,308 A * 11/1995 Hutcheson ......... G06K 9/00221
382/156
7,539,334 B2   5/2009 Corrion
(Continued)

FOREIGN PATENT DOCUMENTS

JP   H11328404 A   11/1999
JP   2003317098 A  11/2003
(Continued)

OTHER PUBLICATIONS

Australian Office Action dated Jul. 27, 2018 issued in counterpart Australian Application No. 2017204494.
(Continued)

*Primary Examiner* — Shervin K Nakhjavan
(74) *Attorney, Agent, or Firm* — Holtz, Holtz & Volek PC

(57) ABSTRACT

Provided are a diagnosis assisting device, an imaging processing method in the diagnosis assisting device, and a non-transitory storage medium having stored therein a program that facilitate a grasp of a difference in an diseased area to perform a highly precise diagnosis assistance. According to an image processing method in a diagnosis assisting device that diagnoses lesions from a picked-up image, a reference image corresponding to a known first picked-up image relating to lesions is registered in a database, and when a diagnosis assistance is performed by comparing a query image corresponding to an unknown second picked-up image relating to lesions with the reference image in the database, a reference image is created from the reference image by geometric transformation, or a query image is created from the query image by geometric transformation.

13 Claims, 11 Drawing Sheets

(51) Int. Cl.
    *G06K 9/46*     (2006.01)
    *G06T 7/62*     (2017.01)
    *G06T 7/11*     (2017.01)
    *G06T 7/33*     (2017.01)
    *A61B 5/00*     (2006.01)

(52) U.S. Cl.
    CPC .............. *G06T 7/11* (2017.01); *G06T 7/337* (2017.01); *G06T 7/62* (2017.01); *A61B 5/0077* (2013.01); *G06T 2207/10024* (2013.01); *G06T 2207/20081* (2013.01); *G06T 2207/20084* (2013.01); *G06T 2207/30088* (2013.01); *G06T 2207/30096* (2013.01)

(56) References Cited

U.S. PATENT DOCUMENTS

| | | | |
|---|---|---|---|
| 7,657,101 B2 | 2/2010 | Christiansen et al. | |
| 7,689,016 B2 | 3/2010 | Stoecker et al. | |
| 7,689,034 B2 | 3/2010 | Terakawa | |
| 8,068,675 B2 | 11/2011 | Christiansen et al. | |
| 8,194,952 B2 | 6/2012 | Mertz et al. | |
| 8,330,807 B2 | 12/2012 | Chen et al. | |
| 8,352,494 B1* | 1/2013 | Badoiu | G06F 16/532 707/772 |
| 8,787,642 B2 | 7/2014 | Li | |
| 9,089,303 B2 | 7/2015 | Chen et al. | |
| 9,286,537 B2 | 3/2016 | Radha Krishna Rao et al. | |
| 9,370,305 B2 | 6/2016 | Qian et al. | |
| 9,418,422 B2 | 8/2016 | Daly et al. | |
| 9,723,270 B2 | 8/2017 | Christiansen et al. | |
| 2004/0009459 A1* | 1/2004 | Anderson | G06F 19/3481 434/262 |
| 2004/0247166 A1* | 12/2004 | Giger | G06F 19/321 382/128 |
| 2006/0210132 A1* | 9/2006 | Christiansen, II | A61B 5/0059 382/128 |
| 2007/0053559 A1 | 3/2007 | Corrion | |
| 2007/0066875 A1* | 3/2007 | Horn | A61B 1/041 600/300 |
| 2007/0292019 A1 | 12/2007 | Terakawa | |
| 2008/0019581 A1* | 1/2008 | Gkanatsios | A61B 6/025 382/131 |
| 2008/0037876 A1* | 2/2008 | Galperin | G06F 19/321 382/203 |
| 2008/0139920 A1* | 6/2008 | Biglieri | A61B 5/055 600/410 |
| 2008/0194928 A1* | 8/2008 | Bandic | G16H 15/00 600/306 |
| 2008/0247619 A1 | 10/2008 | Li | |
| 2009/0304243 A1* | 12/2009 | Mertz | A61B 5/444 382/128 |
| 2010/0111387 A1 | 5/2010 | Christiansen et al. | |
| 2010/0302358 A1 | 12/2010 | Chen et al. | |
| 2010/0318550 A1* | 12/2010 | Yamamoto | G06F 16/532 707/765 |
| 2011/0137132 A1* | 6/2011 | Gustafson | G16H 50/70 600/300 |
| 2011/0273535 A1 | 11/2011 | Mendelson | |
| 2012/0033867 A1* | 2/2012 | Christiansen et al. | |
| 2012/0283574 A1* | 11/2012 | Park | G06K 9/46 600/476 |
| 2013/0218026 A1 | 8/2013 | Chen et al. | |
| 2013/0245417 A1* | 9/2013 | Spector | A61B 5/0013 600/407 |
| 2013/0253337 A1 | 9/2013 | Chen et al. | |
| 2014/0003697 A1 | 1/2014 | Qian et al. | |
| 2014/0125787 A1 | 5/2014 | Christiansen et al. | |
| 2014/0241590 A1* | 8/2014 | Day, Jr. | G01N 15/0205 382/110 |
| 2014/0327702 A1* | 11/2014 | Kreeger | G06T 11/006 345/634 |
| 2015/0206022 A1* | 7/2015 | Radha Krishna Rao | G06K 9/4604 382/128 |
| 2015/0221087 A1 | 8/2015 | Houjou et al. | |
| 2015/0254851 A1 | 9/2015 | Daly et al. | |
| 2015/0310306 A1* | 10/2015 | Song | G06K 9/46 382/159 |
| 2015/0317452 A1* | 11/2015 | Kozuka | G06F 19/321 705/2 |
| 2016/0048651 A1* | 2/2016 | Papier | G06F 19/324 382/128 |
| 2016/0078057 A1* | 3/2016 | Perez de la Coba | G06K 9/6212 707/772 |
| 2017/0011187 A1* | 1/2017 | Oosawa | A61B 6/00 |
| 2017/0116497 A1* | 4/2017 | Georgescu | A61B 6/032 |
| 2017/0124709 A1 | 5/2017 | Rithe et al. | |
| 2017/0148165 A1 | 5/2017 | Houjou et al. | |

FOREIGN PATENT DOCUMENTS

| | | |
|---|---|---|
| JP | 2006350704 A | 12/2006 |
| JP | 2008245719 A | 10/2008 |
| JP | 2010061285 A | 3/2010 |
| JP | 2015164512 A | 9/2015 |
| JP | 2015191286 A | 11/2015 |
| JP | 2016106310 A | 6/2016 |
| WO | 2006078902 A2 | 7/2006 |
| WO | 2013119102 A1 | 8/2013 |
| WO | 2015137542 A1 | 9/2015 |
| WO | 2015175837 A1 | 11/2015 |

OTHER PUBLICATIONS

Extended European Search Report (EESR) dated Nov. 2, 2017 issued in counterpart European Application No. 17179754.1.
Japanese Office Action dated May 22, 2018 (and English translation thereof) issued in counterpart Japanese Application No. 2017-081415.
Japanese Office Action dated Dec. 12, 2017 issued in counterpart Japanese Application No. 2017-081415.
Extended European Search Report (EESR) dated Nov. 19, 2018 issued in European Application No. 18192773.2.
Kawahara, et al., "Deep features to classify skin lesions", 2016 IEEE 13th International Symposium on Biomedical Imaging (ISBI), Apr. 2016, pp. 1397-1400.

* cited by examiner

1 : DIAGNOSIS ASSISTING DEVICE

DIAGNOSIS ASSISTING DEVICE, IMAGE PROCESSING METHOD IN DIAGNOSIS ASSISTING DEVICE, AND NON-TRANSITORY STORAGE MEDIUM HAVING STORED THEREIN PROGRAM

CROSS-REFERENCE TO RELATED APPLICATION

This application claims the benefit of Japanese Patent Application No. 2016-170477, filed on Sep. 1, 2016, and Japanese Patent Application No. 2017-081415, filed on Apr. 17, 2017, of which the entirety of the disclosures is incorporated by reference herein.

FIELD

This application relates generally to a diagnosis assisting device, an image processing method in the diagnosis assisting device, and a storage medium having stored therein a program.

BACKGROUND

Visual check is always carried out for skin lesions, and a medical doctor is capable of obtaining a large quantity of information by visual check. When, however, the visual check is carried out by bare eye or magnifier only, even a distinction between a mole and a fleck is difficult, and a differential diagnosis between a benign tumor and a malignant tumor is also difficult. Hence, dermoscopy diagnosis of picking up an image of diseases using a camera provided with a dermoscope is carried out, but the identification of a case based on an image observation depends on the skill of individual medical doctor under the current circumstances.

Hence, for example, Unexamined Japanese Patent Application Kokai Publication No. 2015-164512 discloses a technology for a medical imaging device capable of creating a high dynamic range synthesis image obtained by a high dynamic range (HDR) imaging conversion from the picked-up image of a patient that has been picked up and stored, and of comparing the high dynamic range synthesis images. According to the technology disclosed in Unexamined Japanese Patent Application Kokai Publication No. 2015-164512, an observation on the dermoscopy image can be easily obtained without a dependency on the diagnosis skill.

SUMMARY

An image processing method in a diagnosis assisting device that diagnoses lesions from a picked-up image, wherein:
a reference image corresponding to a known first picked-up image relating to lesions is registered in a database; and
the method comprises, when a diagnosis assistance is performed by comparing a query image corresponding to an unknown second picked-up image relating to lesions with the reference image in the database:
creating a reference image from the reference image by geometric transformation, or creating a query image from the query image by geometric transformation.

A diagnosis assisting device that diagnoses lesions from a picked-up image, the diagnosis assisting device comprising:
a database to which a reference image corresponding to a known first picked-up image relating to lesions is registered; and
an increaser that creates, when a diagnosis assistance is performed by comparing a query image corresponding to an unknown second picked-up image relating to lesions with the reference image in the database, a reference image from the reference image by geometric transformation, or a query image from the query image by geometric transformation.

BRIEF DESCRIPTION OF THE DRAWINGS

A more complete understanding of this application can be obtained when the following detailed description is considered in conjunction with the following drawings, in which.

DETAILED DESCRIPTION

Figure 1:
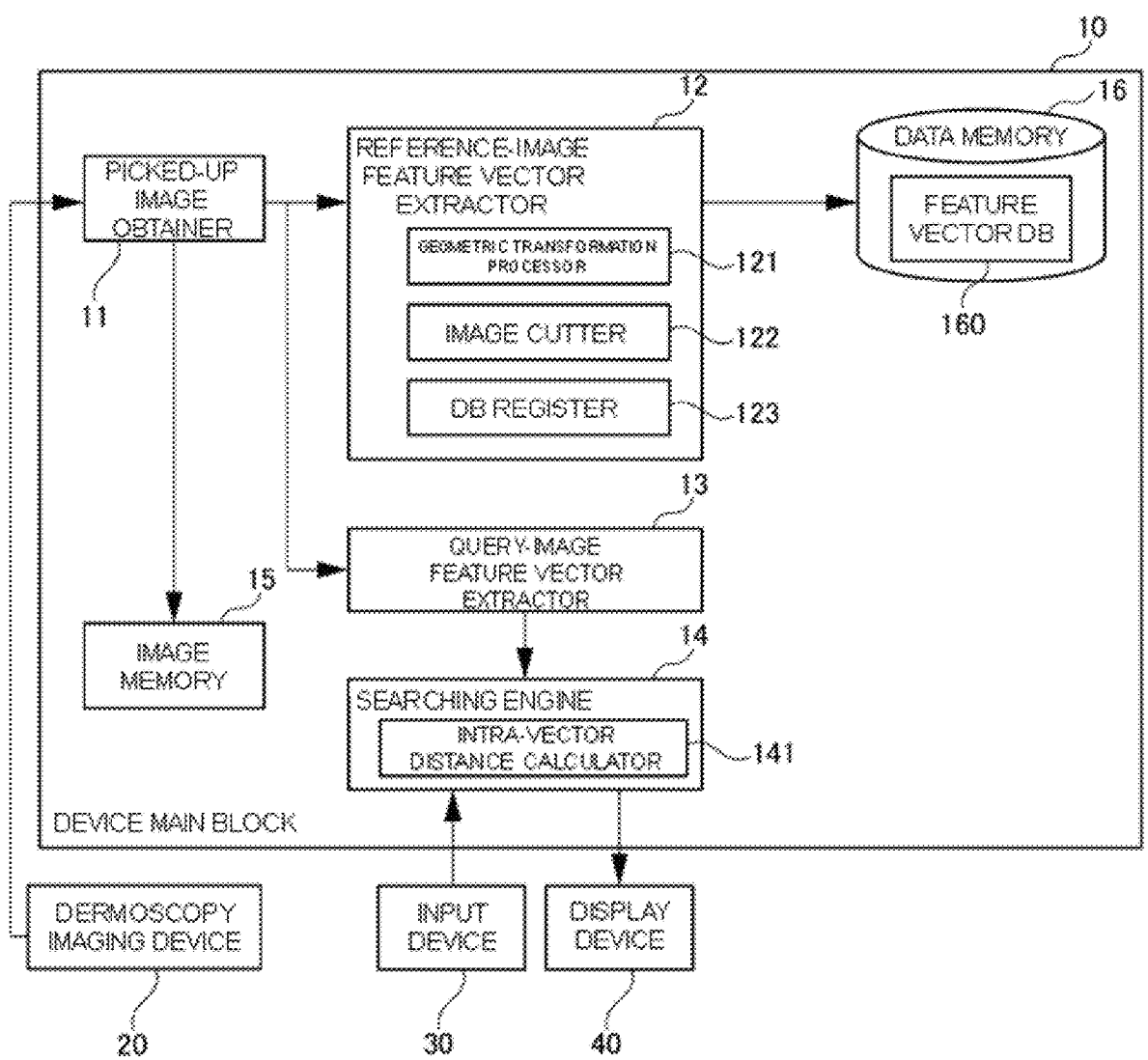
FIG. 1 is a block diagram illustrating a structure of a diagnosis assisting device according to a first embodiment of the present disclosure.

A detailed description will be given of an embodiment to carry out the present disclosure (hereinafter, referred to as an embodiment) with reference to the accompanying figures. In the following figures, the same reference numeral or sign will be given to the same element throughout the entire description for the embodiment.

(Structure: First Embodiment)

FIG. 1 is a block diagram illustrating a structure of a diagnosis assisting device 1 according to a first embodiment. As illustrated in FIG. 1, a dermoscopy imaging device 20 is connected to the diagnosis assisting device 1 of this embodiment.

The dermoscopy imaging device 20 picks up images in accordance with an instruction from a device main block 10 of the diagnosis assisting device 1, stores a picked-up image (dermoscopy image) in an image memory 15, and displays this image on a display device 40. In addition, the device main block 10 performs image processing on the picked-up image, and the processed image is stored in the image memory 15 and also displayed on the display device 40.

An input device 30 is utilized to, for example, instruct the start of dermoscopy-image-pickup, and select a part in a dermoscopy image to be described later. Note that the display device 40 includes, for example, a liquid crystal display (LCD) monitor, and the input device 30 includes, for example, a mouse.

The device main block 10 includes a picked-up image obtainer 11, a reference-image feature vector extractor 12, a query-image feature vector extractor 13, a searching engine 14, the image memory 15, and a data memory 16.

The picked-up image obtainer 11 captures the picked-up image by the dermoscopy imaging device 20, and outputs the captured image to the reference-image feature vector extractor 12, and the query-image feature vector extractor 13. The reference-image feature vector extractor 12 extracts an image feature vector (first image feature vector) with respect to a reference image based on a known image (first picked-up image) relating to lesions, and registers the extracted feature vector in a feature vector database (hereinafter, also referred to as a feature vector DB 160) allocated to a part of the data memory 16. The reference image is created by increase that is geometric transformation (for example, rotation, inversion, resizing) performed on the first picked-up image. Next, by presenting the reference image having undergone the geometric transformation, a diagnosis assistance is carried out. In the following paragraphs, a description will be given of an example case in which the reference image has been increased beforehand, but the increase of the reference image may be performed when compared with a query image. In addition, the increase may be performed on the query image. Still further, the term "present" means to assist a medical doctor by displaying the reference image, and to give a mechanical assist by comparison with the reference image.

Hence, the reference-image feature vector extractor 12 includes a geometric transformation processor 121 (including increaser), an image cutter 122, and a DB register 123.

The geometric transformation processor 121 calculates a first short side actual length of a known picked-up image (first picked-up images) relating to lesions, determines a first resizing increase multiplication factor for the first picked-up image based on the calculated first short side actual length, performs an extrapolation process on the first picked-up image to obtain a first extrapolation image, and performs a geometric transformation process on the first extrapolation image, such as rotation, inversion, and resizing based on the first resizing increase multiplication factor to perform an increase process, thereby obtaining a first geometric transformation image. At this time, the first resizing increase multiplication factor is set to be increase when the first picked-up image is smaller than a total average of the first short side actual lengths, and to be decrease when the first picked-up image is greater than the total average of the first short side actual lengths.

The image cutter 122 obtains a first cutout image by clopping the center square region from the first geometric transformation image output by the geometric transformation processor 121, and extracts an image feature vector (first image feature vector) of the reference image from the first cutout image. The DB register 123 registers, in the feature vector DB 160 of the data memory 16, the first feature vector of the reference image extracted by the image cutter 122.

The query-image feature vector extractor 13 extracts, as for a query image created based on an unknown picked-up image (second picked-up image) relating to lesions, an image feature vector (second image feature vector), and transmits the extracted vector to the searching engine 14.

The searching engine 14 compares the feature vector (first image feature vector) of the reference image with the feature image (second image feature vector) of the query image with reference to the feature vector DB 160, searches at least a candidate that is similar to the query image among the reference images, and outputs the searched candidate to the display device 40. Hence, the searching engine 14 includes an intra-vector distance calculator 141 that calculates a distance (Euclid distance) between the feature vector of the query image and the feature vectors of all reference images registered in the feature vector DB 160.

The image memory 15 stores the dermoscopy image of an affected area picked up by the dermoscopy imaging device 20, and also various pieces of data like images created during the execution of a program according to the first embodiment. The data memory 16 stores the feature vector DB 160 created by the reference-image feature vector extractor 12. Both the image memory 15 and the data memory 16 are provided with memory elements, such as a semiconductor, magnetic, or optical type.

(Action According to First Embodiment)

A detailed description will be given of a process procedure of the diagnosis assisting device 1 according to the first embodiment and illustrated in FIG. 1 with reference to the flowcharts that are FIGS. 2 and 3. First of all, a procedure of a feature-vector creating process by the diagnosis assisting device 1 according to the first embodiment will be described with reference to the flowchart that is FIG. 2.

Note that the feature-vector creating process is executed in an off-line state.

More specifically, first, when a doctor picks up images of an affected area by the dermoscopy imaging device 20 in accordance with an instruction given through the input device 30, the device main block 10 captures picked-up dermoscopy images subjected to the transformation by the picked-up image obtainer 11, stores the captured images in the image memory 15, and also outputs those images to the reference-image feature vector extractor (step S201). In response to this action, the reference-image feature vector extractor 12 causes the geometric transformation processor 121 to calculate the first short side actual length of the image (step S202).

The imaging distance is fixed by the eyepiece adaptor of the dermoscopy imaging device 20, and thus the geometric transformation processor 121 reads and processes device-type information and a focal distance setting from the exchange image file format (EXIF) image file of the picked-up image (first picked-up image), thereby obtaining the short side actual length of the picked-up image.

Figure 4:
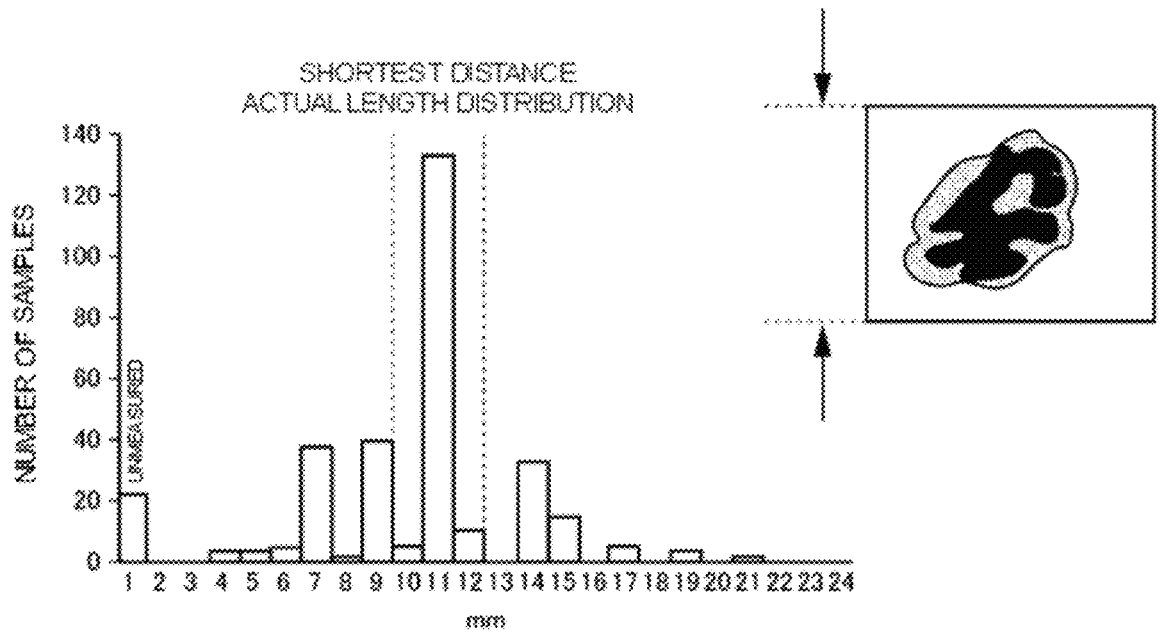
FIG. 4 is an explanatory diagram for a resizing increase policy in a first resizing-increase-multiplication-factor determining process in FIG. 2.

Next, the geometric transformation processor 121 sets the multiplication factor (first resizing increase multiplication factor) for image increase in accordance with the calculated first short side actual length of the picked-up image (step S203). FIG. 4 illustrates a statistical graph that has a vertical axis indicating the number of samples, and a horizontal axis indicating a first short side actual length (mm). According to FIG. 4, the first short side actual lengths are averagely distributed at bin11 (short side 10 to 11 mm). In this case, the data group is classified into three groups, and respective first resizing increase multiplication factors are set. The first resizing increase multiplication factor set by the geometric transformation processor 121 is set in such a way that, in view of the calculated first short side actual length, the smaller first short side actual length than the total average of the first short side actual lengths increases, and the larger first short side actual length than the total average of the first short side actual lengths decreases.

As for a first resizing-increase-multiplication-factor setting process in the step S203, for example, the geometric transformation processor 121 sets three patterns, such as 0.8, 1.0, and 1.2 times when the first short side actual length is close to the total average (equal to or larger than 9 mm and smaller than 12 mm), sets three larger-size patterns, such as 1.0, 1.2, and 1.4 times when the first short side actual length is smaller than the total average (smaller than 9 mm), and sets three smaller-size patterns, such as 0.6, 0.8, and 1.0 times when the first short side actual length is larger than the total average (equal to or larger than 12 mm).

Figure 5:
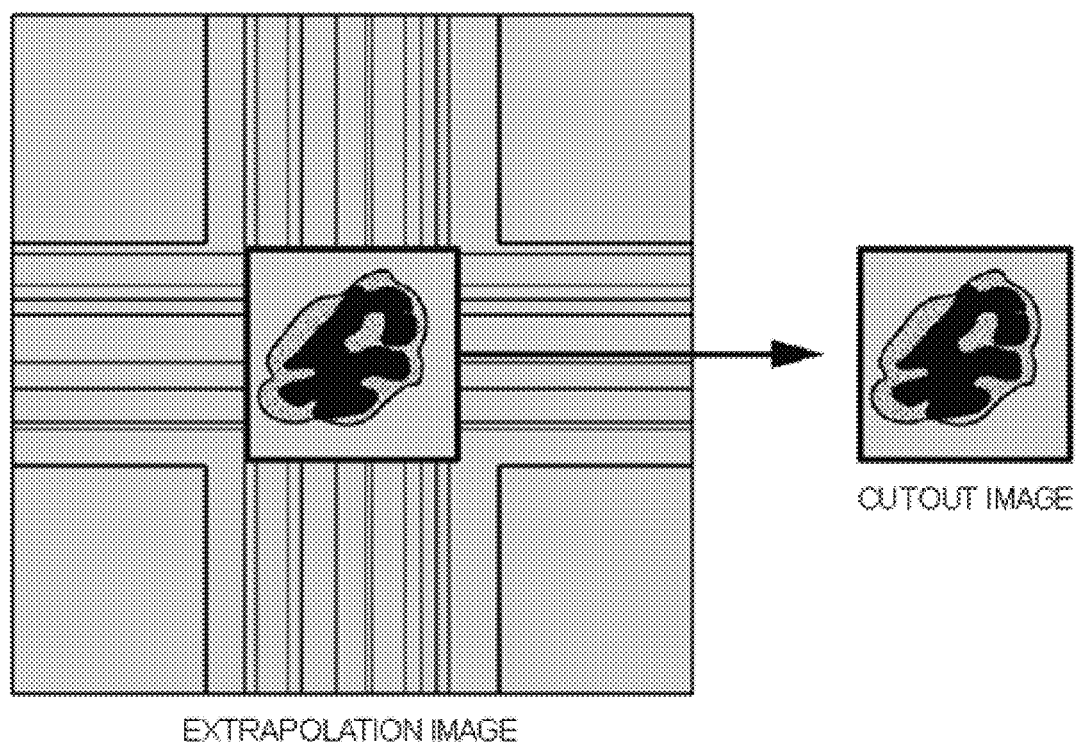
FIG. 5 is a diagram illustrating an example of a first extrapolation image and a first cutout image in an input image extrapolation process in FIG. 2.

Next, the geometric transformation processor 121 executes an extrapolation process on the picked-up image (step S204). That is, when, for example, resizing like zoom-out is executed, an area where the original picked-up image is not present is contained in a valid area, and at this time, a creation of the first extrapolation image is necessary so as to prevent the area where the original picked-up image is not present from becoming an image feature. FIG. 5 illustrates an example of the first extrapolation image.

Subsequently, the geometric transformation processor 121 executes a geometric transformation process on the first extrapolation image, such as rotation, inversion, and resizing (step S205: geometric transformation process involving rotation+inversion+resizing on first extrapolation image). In this case, for example, 16 [turns]×2 [inversions]×3 [multiplication factor]=96 patterns of geometric transformation processes are executed in accordance with, for example, a rotation at an angle per 360 degrees/16, presence/absence of the inversion, and the first resizing increase multiplication factor determined at the step S203, and the control process transitions to the image cutter 122.

The image cutter 122 obtains the geometric transformation process image of the first extrapolation image at the same pixel size as that of the image having undergone the geometric transformation process at the step S205, and for example, as illustrated in FIG. 5, the center square region is clopped, and is taken as a first cutout image (step S206). Next, the desired image feature vector (first image feature vector) is extracted from the clopped image, and is output to the DB register 123. The DB register 123 registers the extracted first image feature vector in the feature vector DB 160 allocated to a partial area of the data memory 16 (step S207: image feature vector extraction+database registration).

The geometric transformation process that involves rotation+inversion+resizing on the first extrapolation image (step S205), the clopping process on the center region having undergone the geometric transformation process (step S206), and the process of image feature vector extraction+database registration (step S207) as explained above are repeatedly executed until the process completes for the images having undergone the 96 patterns of the geometric transformation processes (step S209: YES).

Next, a searching action by the diagnosis assisting device 1 according to the first embodiment will be described with reference to the flowchart that is FIG. 3. In this case, an image search on an unknown query image is executed in an online manner using the feature vector DB 160 which is created in accordance with the flowchart that is FIG. 2 and allocated and stored in a partial area of the data memory 16.

First, under an instruction given through the input device 30 by a doctor, when the dermoscopy imaging device 20 picks up images of an affected area, the device main block 10 causes the picked-up image obtainer 11 to capture an imaged dermoscopy image (second picked-up image) that becomes a search query, and outputs the captured image to the query-image feature vector extractor 13 (step S301). The query-image feature vector extractor 13 executes processes of calculating the second short side actual length of the second extrapolation image, determining the second resizing increase multiplication factor, and extrapolating the picked-up image, and executes the geometric transformation process on the second extrapolation image involving rotation+inversion+resizing thereon, the clopping process on the center area after the geometric transformation process, and the process of extracting the image feature vector like the feature vector creating process on the reference image explained using the flowchart that is FIG. 2, thereby extracting the feature vector (second image feature vector) of the query image, and outputting the extracted feature vector to the searching engine 14 (step S302).

The searching engine 14 causes the intra-vector distance calculator 141 to calculate the intra-vector distance between the query image and the reference image registered in the feature vector DB 160 of the data memory 16 (step S303). In this case, the intra-vector distance calculator 141 calculates, per a sample, an individual Euclid distance for each of 96 reference images already registered in the feature vector DB 160 and increased by the geometric transformation process. Next, each Euclid distance is obtained for each sample, and only the sample that has the shortest distance among those 96 reference images is left (step S304).

Next, the intra-vector distance calculator 141 rearranges the shortest distances of the respective samples in a shorter sequence, sets this rearranged sequence as a search candidate sequence (step S305), and presents, to the display device 40, the candidates of each sample in the search candidate sequence (step S306).

(Effects of First Embodiment)

According to the diagnosis assisting device 1 of the first embodiment, the device main block 10 (reference-image feature vector extractor 12) extracts the image feature vector (first image feature vector) from the reference image increased by performing the geometric transformation process on the known picked-up image (first picked-up image) relating to lesions, and constructs the feature vector DB 160 on the data memory 16. Next, the device main block 10 (query-image feature vector extractor 13) extracts the image feature vector (second feature vector) for the query image formed based on the unknown picked-up image (second picked-up image) relating to lesions, and the searching engine 14 refers to the feature vector DB 160 to compare the image feature vector of the reference image with the image feature vector of the query image, searches at least a candidate similar to the query image among the reference image, and outputs the candidate to the display device 40. Hence, when the doctor visually examines the multiple images arranged side by side, the doctor is facilitated to overview and grasp a difference in diseased area, resulting in a highly precise diagnosis assistance. The images may be displayed and compared one by one (the same is true of the following description).

When the device main block 10 (the reference-image feature vector extractor 12, and the query-image feature vector extractor 13) increases the picked-up image (first and second picked-up images) by performing the geometric transformation process, in view of the calculated first or second short side actual length, the first or second resizing increase multiplication factor is set so as to increase when the first or second short side actual length is smaller than the total average of the first or second short side actual lengths, and is set so as to decrease when the first or second short side actual length is greater than the total average of the first or second short side actual lengths. This decreases an adverse effect irrelevant to the imaging object and not essential to the similarity search like an imaging composition. Hence, when the searched candidate is displayed, the searched candidate can be displayed at the same imaging composition as that of the query image, facilitating a reference and a comparison by visual check. Therefore, the diagnosis assisting device 1 of the first embodiment facilitates a doctor to overview and grasp a difference of diseased area when the multiple images are arranged side by side, thereby accomplishing a highly precise diagnosis assistance.

Figure 6:
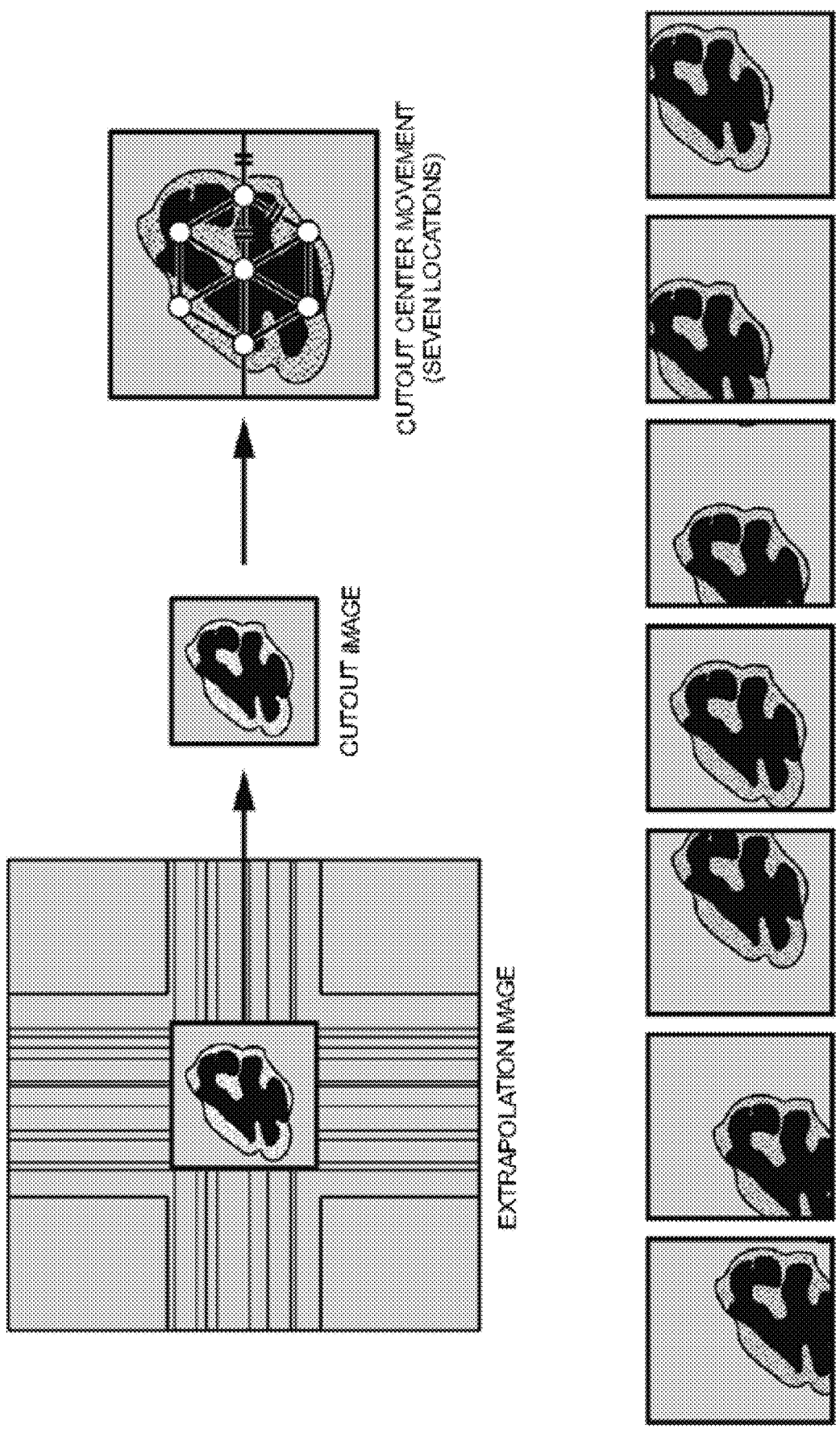
FIG. 6 is a diagram to be referred for describing an expanded example of a geometric transformation process by the diagnosis assisting device according to the first embodiment of the present disclosure.

According to the diagnosis assisting device 1 of the first embodiment, for example, as illustrated in FIG. 5, the number of the first cutout image obtained by clopping the first extrapolation image is one type. However, for example, as illustrated in FIG. 6, by offsetting the cutout position, the number of geometric increase patterns can be increased. More specifically, by shifting the image cutout position (center) at seven locations, seven types of first extrapolation image can be obtained as for the first geometric transformation image. Hence, the geometric transformation increase pattern can be increased, and thus the search precision increases. The points described in this paragraph are also applicable to the second extrapolation image relating to the query image, the second cutout image, and the second geometric transformation image.

In addition, the diagnosis assisting device 1 according to the first embodiment has been described as a stand-alone configuration, but for example, the device main block 10 may be accomplished by a server, and the input device 30 and the display device 40 may be accomplished by terminals connected to the server via a network like Internet protocol (IP). In this case, a client-server system is accomplished such that, when the server receives a search query from the terminal, the server compares the search query with the feature vectors stored in the feature vector DB 160, searches at least a candidate similar to the query image, and the candidate is output to the requesting terminal.

The image processing method according to the first embodiment is, for example, as illustrated in FIG. 1, an image processing method in the diagnosis assisting device 1 to diagnose lesions from the picked-up images. This image processing method includes, for example, (A) creating a database to which a first image feature vector extracted for the reference image created based on the known first picked-up image relating to lesions is registered, and (B) extracting a second image feature vector for the query image created based on an unknown second picked-up image relating to the lesions, referring to the database to compare the second image feature vector with the first image feature vectors, and searching at least a candidate similar to the query image among the reference images, and in (A) creating the database, the reference image is created by performing the geometric transformation on the first picked-up image for increase.

Figure 2:
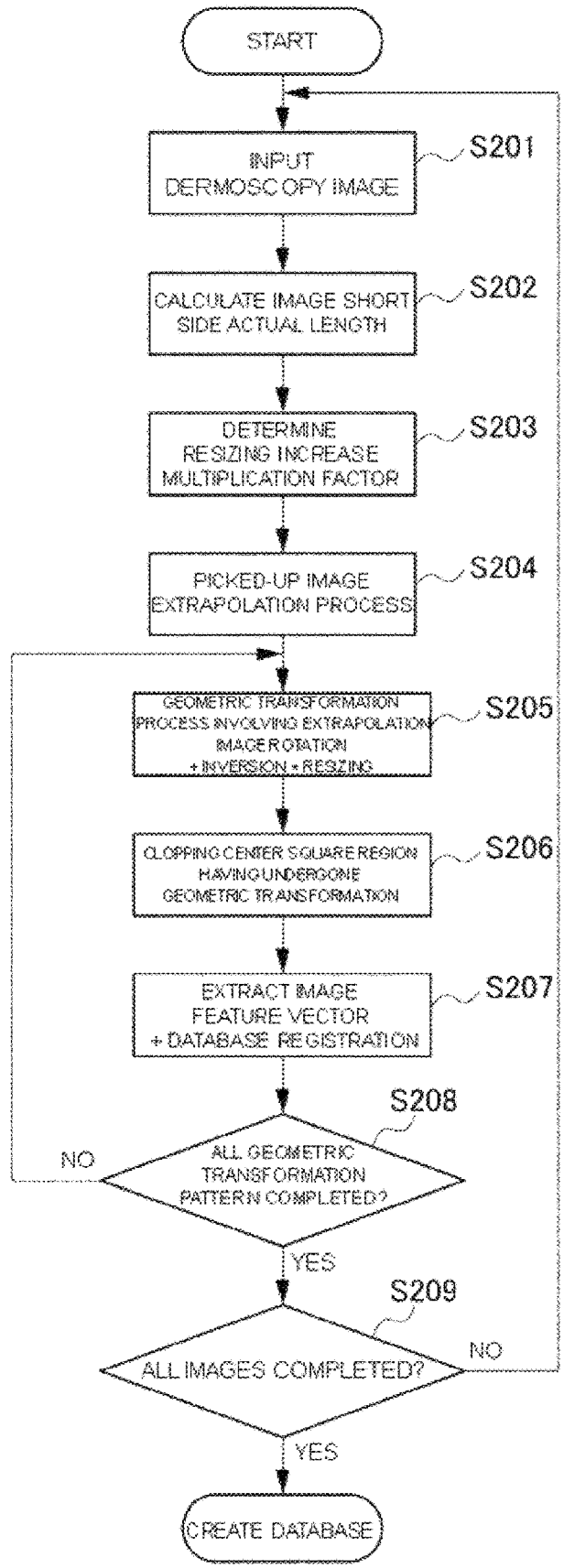
FIG. 2 is a flowchart illustrating a procedure of a feature-vector database creating process by the diagnosis assisting device according to the first embodiment of the present disclosure.
Figure 3:
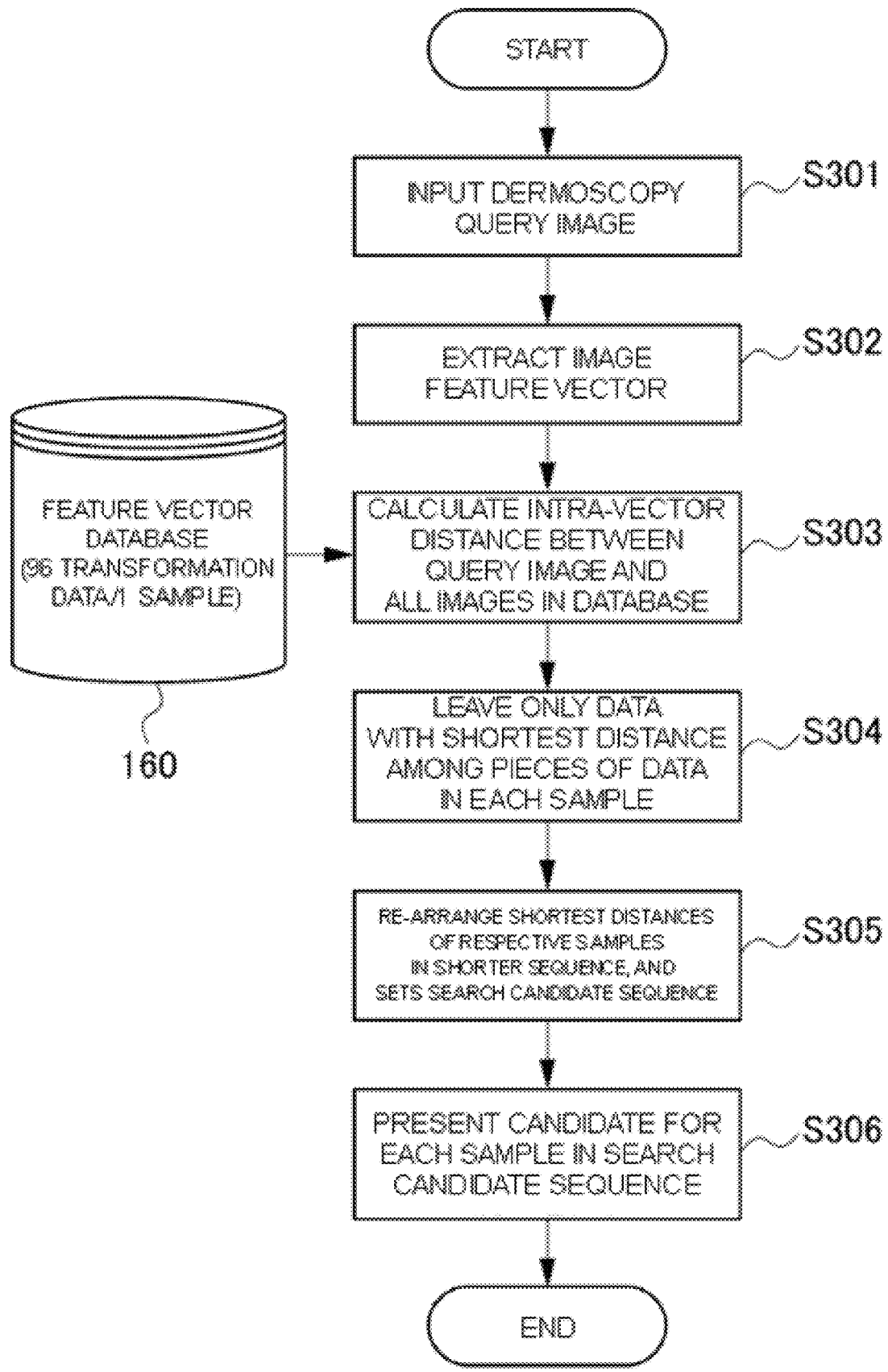
FIG. 3 is a flowchart illustrating a procedure of an image searching process by the diagnosis assisting device according to the first embodiment of the present disclosure.

In this case, the action (A) corresponds to the steps S201 to S209 in the flowchart that is FIG. 2, and the action (B) corresponds to the steps S301 to S306 in the flowchart that is FIG. 3.

In addition, in the image processing method according to the first embodiment, (A) creating the database may include (A2) inputting the first picked-up image, (A3) calculating a first short side actual length of the first picked-up image, (A4) determining a first resizing increase multiplication factor for the first picked-up image using the first short side actual length, (A5) performing an extrapolation process on the first picked-up image to obtain a first extrapolation image, (A6) increasing the first extrapolation image by a geometric transformation process involving rotation, inversion and resizing based on the first resizing increase multiplication factor to obtain a first geometric transformation image, (A7) obtaining a first cutout image by clopping a center square region from the first geometric transformation image, and (A8) extracting and registering a first image feature vector from the first cutout image.

In this case, in FIG. 2, the action (A2) corresponds to the step S201, the action (A3) corresponds to the step S202, the action (A4) corresponds to the step S203, the action (A5) corresponds to the step S204, the action (A6) corresponds to the step S205, the action (A7) corresponds to the step S206, and the action (A8) corresponds to the step S207.

(B) searching may include (B2) inputting the second picked-up image, (B3) calculating a second short side actual length of the second picked-up image, (B4) determining a second resizing increase multiplication factor for the second picked-up image using the second short side actual length, (B5) performing an extrapolation process on the second picked-up image to obtain a second extrapolation image, (B6) increasing the second extrapolation image by a geometric transformation process involving rotation, inversion and resizing based on the second resizing increase multiplication factor to obtain a second geometric transformation image, (B7) obtaining a second cutout image by clopping a center square region from the second geometric transformation image, (B8) extracting the second image feature vector from the second cutout image, (B9) calculating an intra-vector distance between the second image feature vector and the first image feature vector, (B10) obtaining the intra-vector distance for each sample of the first image feature vector, and leaving only the sample with the shortest distance, (B11) arranging the shortest distances of the respective samples in a shorter sequence to obtain a search candidate sequence, and (B12) presenting the candidate for each sample in the search candidate sequence.

In this case, the actions (B2) to (B8) correspond to the actions (A2) to (A8), and in FIG. 3, the action (B2) corresponds to step S301, and the actions (B3) to (B8) correspond to the step S302, respectively. In addition, in FIG. 3, the action (B9) corresponds to the step S303, the action (B10) corresponds to the step S304, the action (B11) corresponds to the step S305, and the action (B12) corresponds to the step S306, respectively.

According to the image processing method of the first embodiment, when an observation is to be obtained by visual check on multiple images arranged side by side, a difference in an diseased area can be easily overviewed and grasped, and thus a highly precise diagnosis assistance can be accomplished.

A program according to the first embodiment is, for example, as illustrated in FIG. 1, a program for the image processing method in the diagnosis assisting device 1 to diagnose lesions from a picked-up image. In this case, this program causes a computer (device main block 10) to execute the similar processes to the actions involved in the image processing method according to the first embodiment.

Hence, a description of each process will not be repeated so as to avoid a redundant description below.

According to the program of the first embodiment, when an observation is to be obtained by visual check on multiple images arranged side by side, the device main block 10 reads and executes the program according to the first embodiment to facilitate an overview and a grasp on a difference in an diseased area, and thus a highly precise diagnosis assistance is accomplished. The program according to the first embodiment is stored in an unillustrated program memory in the device main block 10.

(Second Embodiment)

Next, a second embodiment will be described. According to conventional machine learning based on an input of a square image, since geometric increase is performed based a low-resolution image obtained by resizing a rectangular image into a square image, cutting sides beforehand to obtain a square image, and the like, there is a technical problem such as an image quality deterioration. Hence, according to the second embodiment, when machine learning is performed on an input of a low-resolution square image using an identifier including a neural network, a highly precise learning is performed while maintaining the reduction of the image information as minimum as possible. More specifically, from a high-resolution rectangular image, low-resolution square image having multiple patterns of rotation angle and multiplication factors changed beforehand is prepared. Next, at the time of machine learning, by performing an online geometric increase involving a 90-degree rotation and an inversion that do not deteriorate the image quality on the image prepared beforehand, thereby performing a highly precise learning while maintaining the reduction of the image information as minimum as possible. Next, the similar geometric increase is performed at the time of inference by the identifier, and thus the multiple inference values by what corresponds to the increase are averaged to obtain an eventual inference value.

Figure 7:
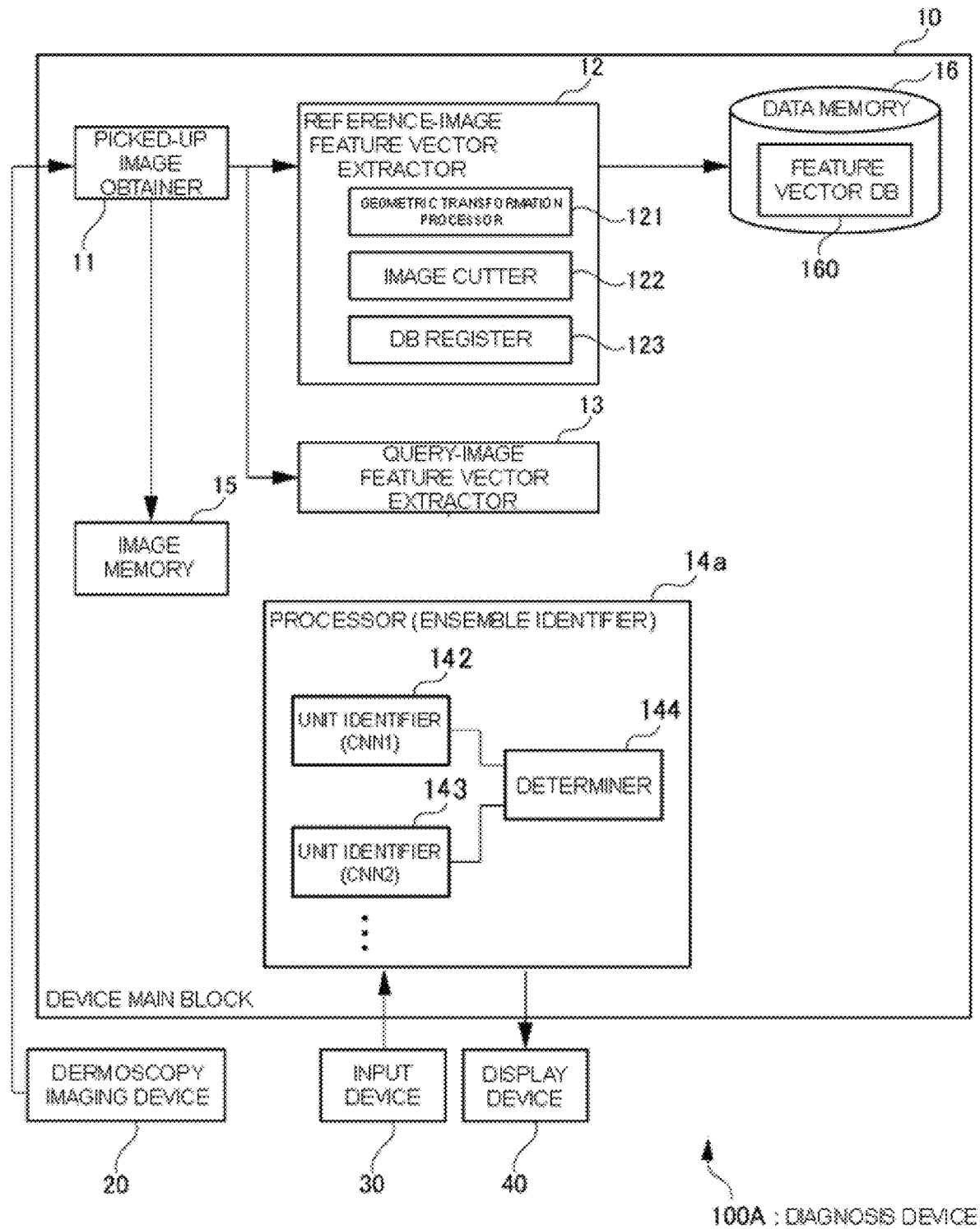
FIG. 7 is a block diagram illustrating a structure of the diagnosis assisting device according to a second embodiment of the present disclosure.

FIG. 7 is a block diagram illustrating a structure of a diagnosis assisting device according to the second embodiment of the present disclosure. As illustrated in FIG. 7, a diagnosis device 100A according to the second embodiment of the present disclosure is connected to the dermoscopy imaging device 20.

The dermoscopy imaging device 20 picks up an image in accordance with an instruction from the diagnosis device 100A, stores the picked-up image (dermoscopy image) in the image memory 15, and displays on the display device 40. In addition, the picked-up image is subjected to the image processing by a diagnosis assisting device main block 10, and is stored in the image memory 15, and also displayed on the display 40.

The input device 30 is to instruct a start of a dermoscopy image pickup, and to select a part within the dermoscopy image to be described later, and the like. The display device 40 includes, for example, an LCD, and the input device 30 includes a mouse, and the like.

The data memory 16 stores not only the feature vector DB 160 created by the reference-image feature vector extractor 12 but also a skin image database that stores identification names for diseases for the purpose of learning and known skin image data in association with each other.

A diagnosis device main block 10a includes the reference-image feature vector extractor 12, the query-image feature vector extractor 13, an ensemble identifier 14a, and the picked-up image obtainer 11. The reference-image feature vector extractor 12 and the query-image feature vector extractor 13 employ the same structures as those of the first embodiment, and thus the detailed explanation thereof will not be repeated, but in the second embodiment, in the geometric transformation processor 121, a low-resolution square image that has multiple patterns of rotation angle and multiplication factor changed from a high-resolution rectangular image is prepared beforehand and the low-resolution square image is to be input for machine learning by the ensemble identifier 14a to be described later.

The low-resolution square image prepared beforehand is input to the ensemble identifier 14a. The ensemble identifier 14a identifies whether or not an check object is any of diseases based on multiple unknown skin image data relating to the object to be diagnosed and pre-processed. The ensemble identifier 14a includes at least two unit identifiers 142(CNN1) and 143(CNN2), so as to correspond to multiple pieces of the skin image data containing at least two of original image data relating to the object, the "first conversion image data" converted from the original image data, and the "second conversion image data" likewise converted from the original image data, and a determiner 144 integrating the identification values obtained by the respective unit identifiers 142, 143, and the like, and obtaining an eventual determination value.

The unit identifier 142, 143, and the like, includes a convolutional neural network (CNN) that performs learning based on the multiple pieces of known skin image data relating to diseases, and the learning is performed beforehand by inputting the conversion image data created by the geometric transformation processor 121 into this convolutional neural network, and thus a function of an identifier that creates classification information enabling identification of diseases to be diagnosed.

The unit identifiers 142, 143, and the like, may perform learning beforehand prior to the shipping of the diagnosis device 100A from a manufacturing factory, or may perform learning beforehand after the shipping at a hospital, or the like. The term "beforehand" in this case means a time point prior to identification of diseases to be diagnosed.

Figure 8:
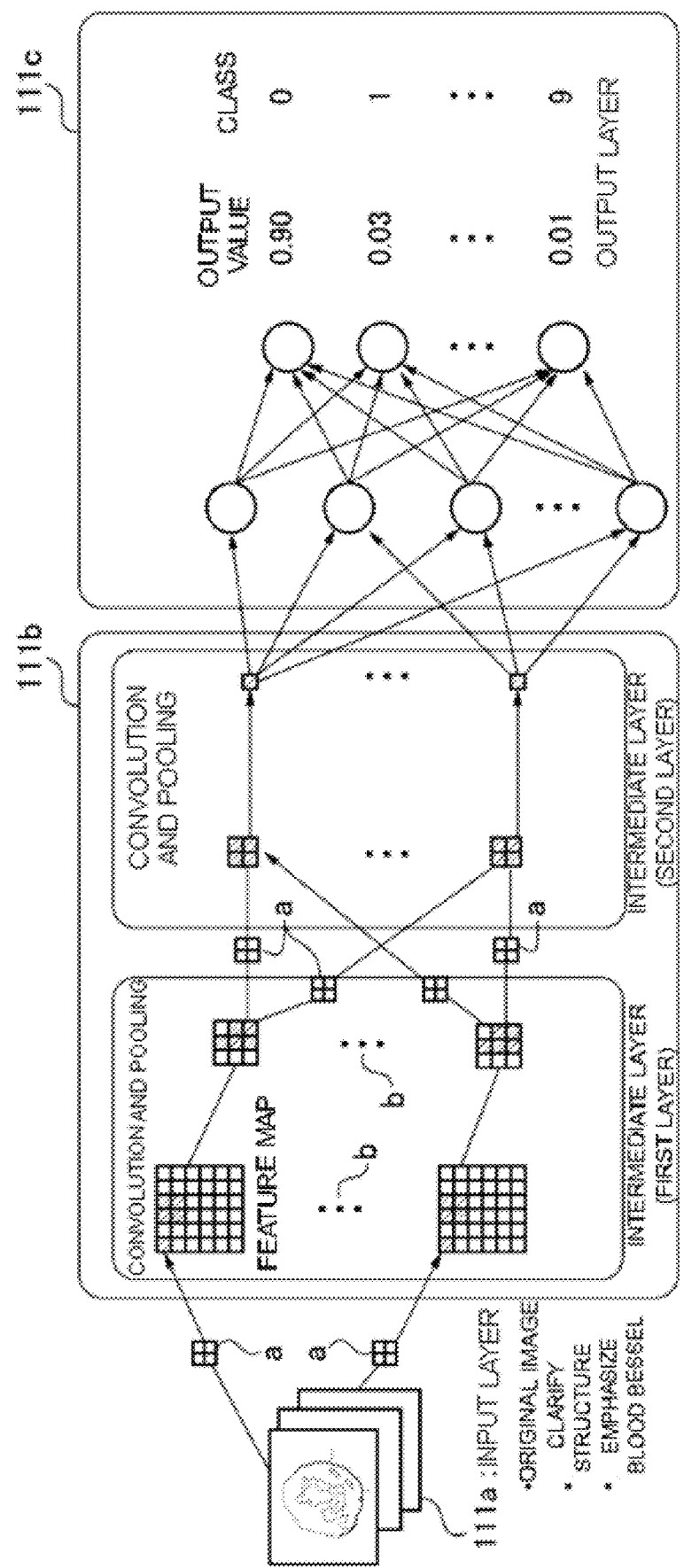
FIG. 8 is a block diagram illustrating a structure of an ensemble identifier (neural network) according to the second embodiment of the present disclosure.

FIG. 8 illustrates a representative structure of a convolutional neural network (CNN). In FIG. 8, the convolutional neural network includes an input layer 111a into which multiple pieces of known skin image data (conversion image data) are input at the learning stage, and into which multiple pieces of unknown skin image data (conversion image data) are input at an check stage, an intermediate layer 111b that includes multiple sets of convolution layers and pooling layers, and extracts a feature from the multiple pieces of known skin image data or the multiple pieces of unknown skin image data, and an output layer 111c that outputs an identification value for each classification of the diagnosis object based on the extracted feature.

The process of the convolutional neural network is executed via multiple process units a connected in a multi-stage manner. The input and output as for each process unit a are multiple two-dimensional image indicated by a feature map b that is multiple features extracted from the input image. In this case, the input image is regarded as a sheet of feature quantity map. In this case, a pair of convolution arithmetic processing unit and pooling unit is connected as the process unit a, and the multiple process units a are connected in a multi-stage manner. Each process unit a calculates a feature quantity vector. The determiner 144 to be described later performs an identifying process on this feature quantity vector, and thus an output class is obtained.

The determiner 144 has the extracted feature input thereto, and identifies the feature. The learning by the convolutional neural network updates the weighting of each layer by learning based on a backpropagation scheme. A multi-layer perceptron is applied as the identifying process. The multi-layer perceptron includes the input layer 111a, the intermediate layer 111b, and the output layer 111c. This is a non-linear class identifier. The weighting between each layer is obtained by stochastic gradient descent based on the backpropagation scheme. At the time of identification, the feature quantity is propagated in sequence, and the image is classified with the output by each unit of the output layer being as a post-probability of each class. In this case, the identification values obtained by the respective unit identifiers 142, 143, and the like, are integrated so as to obtain the eventual determination value.

The convolutional neural network is a general scheme to highly precisely classify images, and details are described at, for example, the Internet URL (http://en.wikipedia.org/wiki/Convolutional neural network). The convolutional neural network (CNN) is a type of deep learning (deep neural network: DNN) that performs learning with a multi-layer structure of a neural network that simulates a brain neural circuit network, and is suitably applicable to image analysis. Other schemes than the deep learning are also applicable, and the deep learning may be combined with the other schemes.

The picked-up image obtainer 11 is capable of obtaining multiple pieces of unknown skin image data, and outputs the skin image data to the query-image feature vector extractor 13 for the purpose of image conversion like structure clarification, partial emphasis, and the like.

(Action of Second Embodiment)

A detailed description will be given of an action of the diagnosis device 100A according to the second embodiment of the present disclosure with reference to the flowcharts that are FIGS. 9 to 12. FIGS. 9, 10, 11, and 12 respectively illustrate the sequence of an image pre-increase process, an example of a geometric transformation pattern for image pre-increase, a learning procedure of causing the ensemble identifier 14a to perform machine learning (neural network) using the image pre-increase process, and an inference procedure using the ensemble identifier 14a that has already performed learning. The following action can be configured as a learning process program to be executed by a computer.

Figure 9:
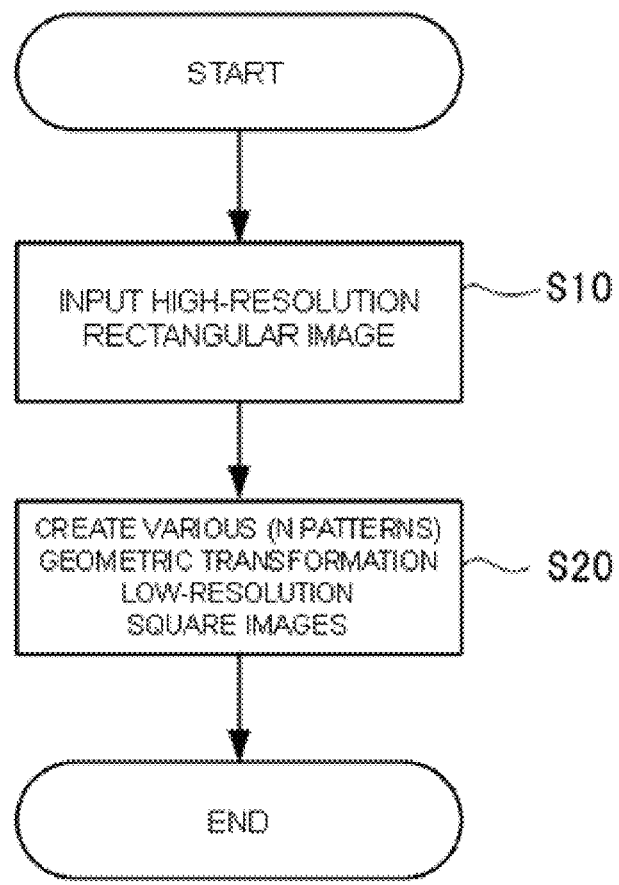
FIG. 9 is a flowchart for an image pre-increase according to the second embodiment of the present disclosure.

First, as illustrated in FIG. 9, a pre-increase is performed on the picked-up image. That is, a high-resolution rectangular image that is a typical picked-up image is input to the diagnosis assisting device 100A (step S10). Next, the image is subjected to geometric transformation, and multiple patterns of predetermined low-resolution square image (for example, 224 by 224) are created (step S20). That is, a square image (224 by 224) is prepared beforehand, and within the neural network of the ensemble identifier 14a, only increase that involves 90×L degree rotation and inversion that do not deteriorate the image is performed. In this case, L is an integer of 0 to 3, and 90×L degrees indicate 0 degree, 90 degrees, 180 degrees, and 270 degrees.

Figure 10:
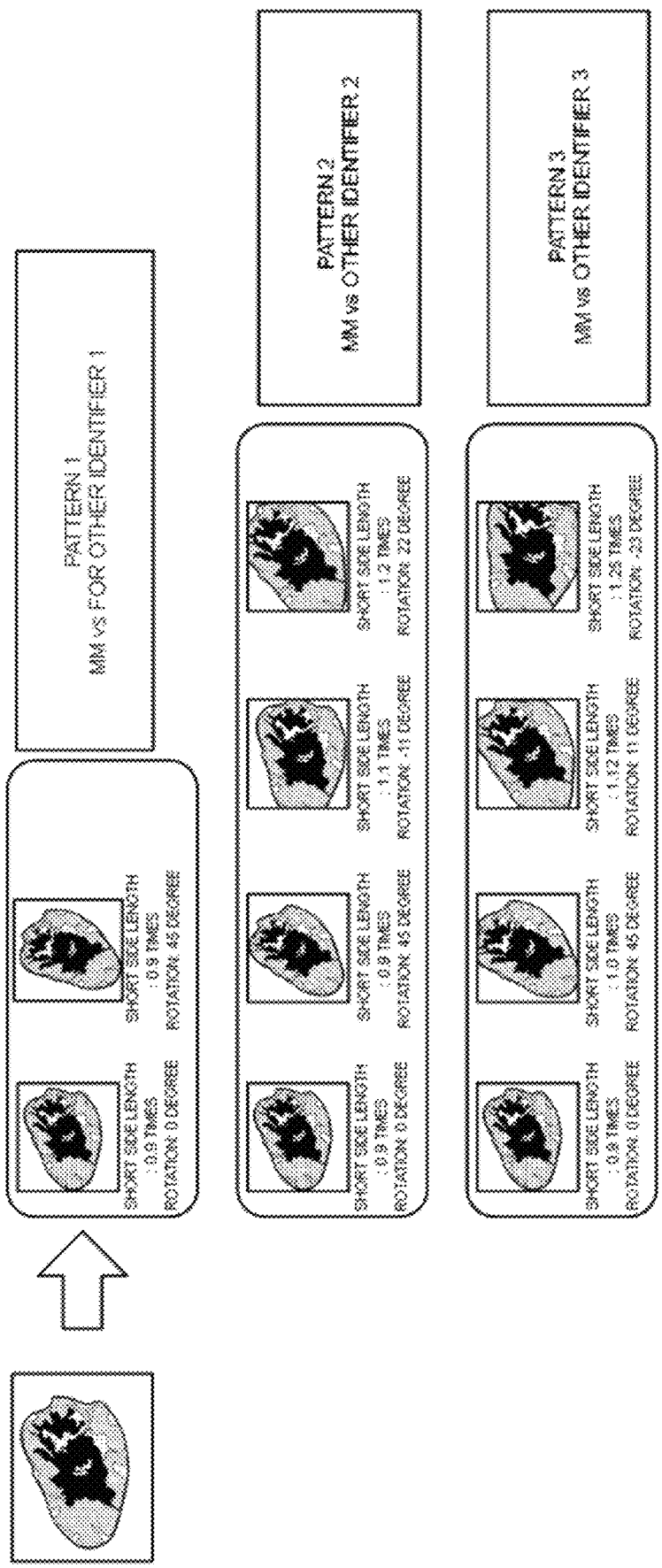
FIG. 10 is an explanatory diagram for an example of a geometric transformation pattern for the image pre-increase according to the second embodiment of the present disclosure.

FIG. 10 illustrates a specific example of geometric transformation. The geometric transformation is performed by rotation of the image and by elongation and compression of the short side length. According to the pattern 1 illustrated at the upper part of FIG. 10, the image is rotated by 0 degree or by 90 degrees for a single unit identifier, and then transformation is performed so as to obtain both short sides of the original images that are 224 by 0.9 pixels. According to the pattern 2 illustrated at the middle part, the image is rotated by 0 degree, 45 degrees, −11 degrees or −22 degrees for the other unit identifier, and then transformation is performed so as to obtain the respective short sides of the original images that are 224 by 0.9 pixels, 224 by 0.9 pixels, 224 by 1.1 pixels, and 224 by 1.2 pixels. According to the pattern 3 illustrated in the lower part, the image is rotated by 0 degree, 45 degrees, 11 degrees or −23 degrees for the further other unit identifier, and then transformation is performed so as to obtain the respective short sides of the original images that are 224 by 0.9 pixels, 224 by 1.0 pixels, 224 by 1.12 pixels, and 224 by 1.25 pixels. When the short side is multiplied by 0.9 times, since the original image does not fall in the 224 pixel size, an appropriate extrapolation process is executed. In addition, in FIG. 10, an example case is described in which there are the three identifiers, but at least two unit identifiers may be provided, and in conclusion, the geometric transformation is performed based on the different pattern for each unit identifier.

Figure 11:
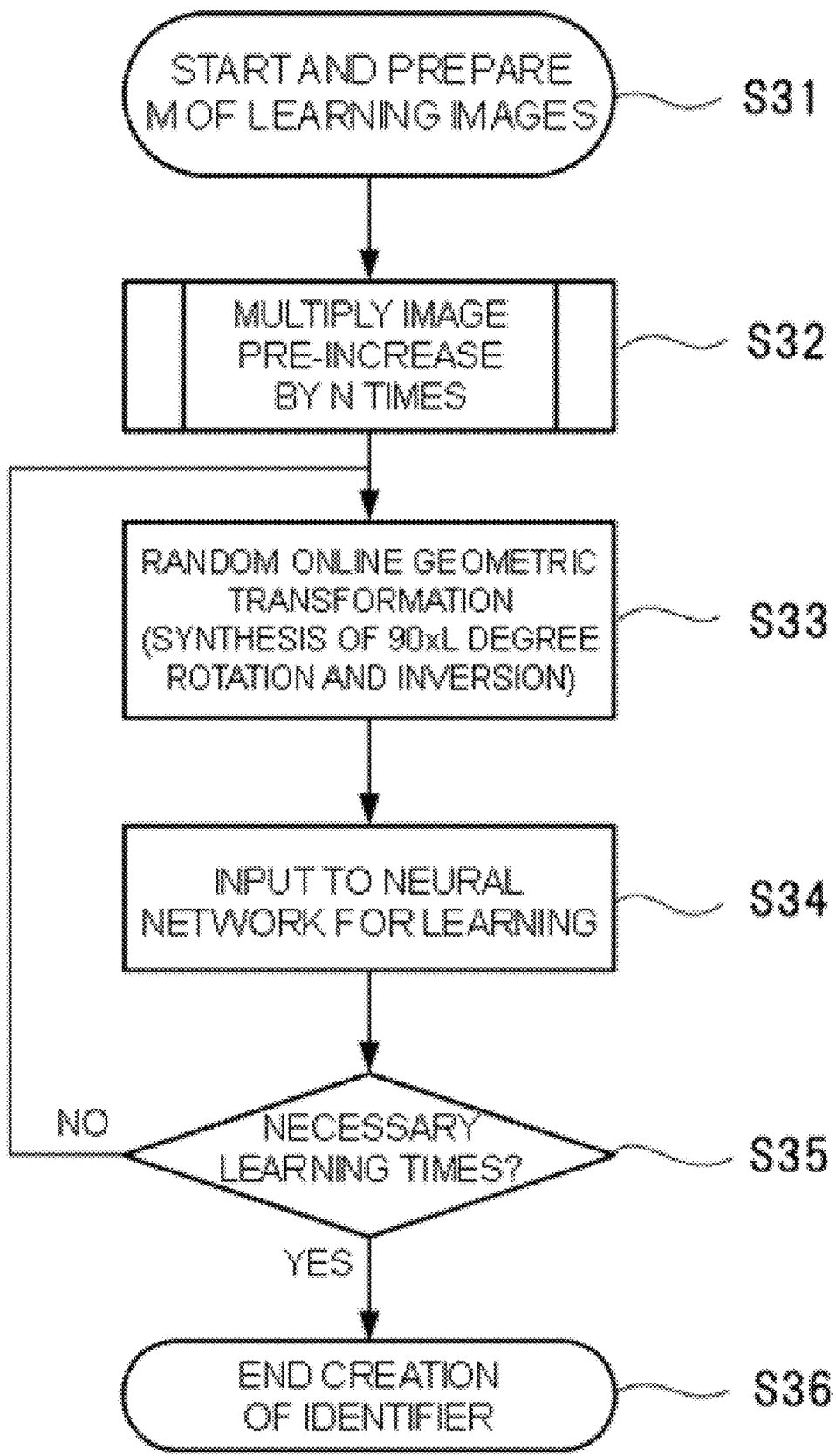
FIG. 11 is a flowchart illustrating a flow of a machine learning identifier creating process according to the second embodiment of the present disclosure.

The machine learning by the ensemble identifier 14a is performed in accordance with the following procedure illustrated in FIG. 11. First, multiple pieces (M) of learning images (reference images) are prepared for machine learning (step S31). Next, in the procedure illustrated in FIG. 9, the learning image is pre-increased for N patterns, and thus M×N of the learning images are obtained (step S32). Among those M×N of the learning images, a predetermined image is taken out, and rotation by 90×L degrees and inversion or non-inversion are performed at random (step S33). Next, those increased images are input to the neural network for learning (step S34). A determination is made on whether or not the number of repeated times reaches the necessary number for learning (step S35), and the procedures at the step S33 and the step S34 are repeated. When the necessary number for learning is accomplished, the ensemble identifier 14a that has already performed learning is created (step S36). In this case, M and N are integers equal to or greater than 2.

Figure 12:
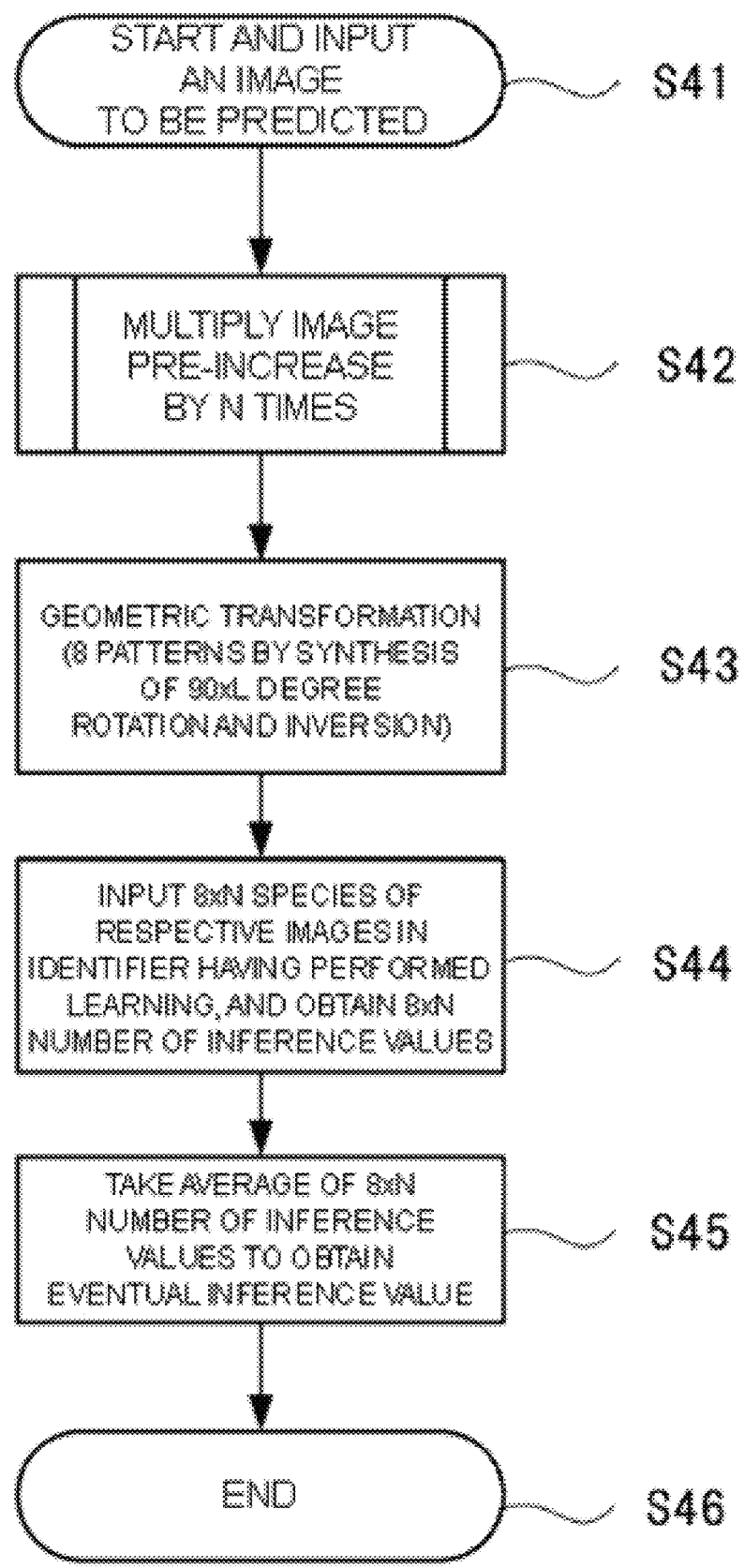
FIG. 12 is a flowchart illustrating a flow of a suspected image (unknown image) identifying process according to the second embodiment of the present disclosure.

Using the ensemble identifier 14a that has already performed learning and created by the procedure illustrated in FIG. 11, an identification (inference) of the unknown picked-up image (query image) is performed through the following procedure illustrated in FIG. 12. First, an unknown image to be predicted is input (step S41). Next, through the same procedure as that of FIG. 9, the unknown picked-up image is pre-increased by N patterns, and thus N of images are obtained (step S42). As for each of N of the images, 8 patterns of geometric transformation are performed based on a combination of 90×L degree rotation and inversion or non-inversion, and thus 8×N of the images are created (step S43). Next, each of 8×N of the images is individually input to the ensemble identifier 14a, thereby obtaining 8×N of the inference values are obtained (step S44). Eventually, 8×N of the inference values are averaged, and thus an eventual inference value is obtained (step S45). Through the above procedure, the inference is completed (step S46).

As for an expanded application of the second embodiment, for example, the value learnt and inferred based on the pattern 1 in FIG. 10 and the value learnt and inferred based on the pattern 2 or pattern 3 may be averaged to obtain an eventual inference value.

(Effects of Second Embodiment)

By preparing an image having undergone rotation and resizing from a high-resolution image beforehand, an occurrence of an image quality deterioration by magnification and a non-continuous part by rotation, and the like, can be suppressed, and thus the loss of original image information can be minimized.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

More specifically, the above embodiments are described with example lesions relating to skin, but the present disclosure is applicable to other lesions than skin, such as eyeground, and an organ like uterus.

What is claimed is:

1. An image processing method in a diagnosis assisting device that diagnoses lesions from a picked-up image, wherein:
    a reference image corresponding to a known first picked-up image relating to lesions is registered in a database; and
    the method comprises, when diagnosis assistance is performed by comparing a query image corresponding to an unknown second picked-up image relating to lesions with the reference image in the database:
        calculating a first short side actual length of the first picked-up image;
        determining a first resizing increase multiplication factor for the first picked-up image using the first short side actual length;
        performing an extrapolation process on the first picked-up image to obtain a first extrapolation image;
        performing a geometric transformation process on the first extrapolation image involving rotation, inversion, and resizing based on the first resizing increase multiplication factor to obtain a first geometric transformation image; and
        obtaining a first cutout image as the reference image by cropping a center square region from the first geometric transformation image, and extracting a first image feature vector from the first cutout image.

2. The image processing method according to claim 1, wherein the first resizing increase multiplication factor is set such that a first short side actual length that is smaller than a total average of first short side actual lengths increases, and such that a first short side actual length that is larger than the total average of the first short side actual lengths decreases.

3. The image processing method according to claim 1, further comprising:
    extracting a second image feature vector for a query image created based on the unknown second picked-up image relating to lesions; and
    comparing the second image feature vector with the first image feature vector, and searching at least a candidate similar to the query image from among plural reference images.

4. An image processing method in a diagnosis assisting device that diagnoses lesions from a picked-up image, wherein:
    a reference image corresponding to a known first picked-up image relating to lesions is registered in a database; and
    the method comprises, when diagnosis assistance is performed by comparing a query image corresponding to an unknown second picked-up image relating to lesions with the reference image in the database:
        extracting a first image feature vector for a reference image created by performing geometric transformation on the first picked-up image for increase;
        calculating a second short side actual length of the second picked-up image;
        determining a second resizing increase multiplication factor for the second picked-up image using the second short side actual length;
        performing an extrapolation process on the second picked-up image to obtain a second extrapolation image;
        performing a geometric transformation process on the second extrapolation image involving a rotation, an inversion, and a resizing based on the second resizing increase multiplication factor to obtain a second geometric transformation image;
        obtaining a second cutout image by cropping a center square region from the second geometric transformation image, and extracting a second image feature vector from the second cutout image; and
        comparing the second image feature vector with the first image feature vector, and searching at least a candidate similar to the query image from among plural reference images.

5. The image processing method according to claim 4, wherein the second resizing increase multiplication factor is set such that a second short side actual length that is smaller than a total average of second short side actual lengths increases, and such that a second short side actual length that is larger than the total average of the second short side actual lengths decreases.

6. An image processing method in a diagnosis assisting device that diagnoses lesions from a picked-up image, wherein:
    a reference image corresponding to a known first picked-up image relating to lesions is registered in a database; and
    the method comprises, when diagnosis assistance is performed by comparing a query image corresponding to an unknown second picked-up image relating to lesions with the reference image in the database:
        extracting a second image feature vector for the query image created based on the second picked-up image, comparing the second image feature vector with a first image feature vector extracted for the reference image created based on the first picked-up image, and searching at least a candidate similar to the query image from among plural reference images,
        wherein the extracting comprises extracting the second image feature vector from a second geometric transformation image obtained by geometrically transforming and increasing the second picked-up image, or from a second cutout image obtained by cropping a center square region from the second geometric transformation image, calculating an intra-vector distance between the first image feature vector and the second image feature vector for each sample of the first image feature vector, arranging the shortest distances of the respective samples in a shorter sequence to obtain a search candidate sequence, and presenting the candidate for each sample.

7. An image processing method in a diagnosis assisting device that diagnoses lesions from a picked-up image, wherein:
    a reference image corresponding to a known first picked-up image relating to lesions is registered in a database; and the method comprises, when diagnosis assistance is performed by comparing a query image corresponding to an unknown second picked-up image relating to lesions with the reference image in the database:
preparing, beforehand, a low-resolution square image from a high-resolution rectangular image that is the first picked-up image; and
performing geometric increase on the low-resolution square image and inputting the increased image in a neural network for machine learning, and creating an ensemble identifier.

8. The image processing method according to claim 7, wherein:
the ensemble identifier comprises a plurality of unit identifiers; and
at least one of the reference image and the query image is subjected to geometric transformation based on different pattern for each of the unit identifiers.

9. An image processing method in a diagnosis assisting device that diagnoses lesions from a picked-up image, wherein:
a reference image corresponding to a known first picked-up image relating to lesions is registered in a database; and
the method comprises, when diagnosis assistance is performed by comparing a query image corresponding to an unknown second picked-up image relating to lesions with the reference image in the database:
preparing, beforehand, a low-resolution square image from a high-resolution rectangular image that is the second picked-up image; and
performing geometric increase on the low-resolution square image and inputting the increased image in a neural network for machine learning, and creating an ensemble identifier.

10. An image processing method in a diagnosis assisting device that diagnoses lesions from a picked-up image, wherein:
a reference image corresponding to a known first picked-up image relating to lesions is registered in a database; and
the method comprises, when diagnosis assistance is performed by comparing a query image corresponding to an unknown second picked-up image relating to lesions with the reference image in the database:
with respect to the reference image:
preparing M of the first picked-up images for machine learning;
pre-increasing the first picked-up image for N patterns to obtain M×N of the first picked-up images;
picking up a predetermined image from the M×N of the first picked-up images for learning, and performing random geometric transformation involving 90×L degree rotation and inversion or non-inversion;
inputting the first picked-up image having undergone geometric transformation into a neural network for machine learning; and
repeating the geometric transformation and machine learning until a number of repeated times reaches a necessary time to create an identifier, wherein M and N are each an integer equal to or greater than 2, and L is an integer from 0 to 3, inclusive.

11. The image processing method according to claim 10, further comprising:
inputting a high-resolution rectangular image as the first picked-up image; and
preparing, beforehand, a low-resolution square image from the high-resolution rectangular image.

12. An image processing method in a diagnosis assisting device that diagnoses lesions from a picked-up image, wherein:
a reference image corresponding to a known first picked-up image relating to lesions is registered in a database; and
the method comprises, when diagnosis assistance is performed by comparing a query image corresponding to an unknown second picked-up image relating to lesions with the reference image in the database:
with respect to the query image:
inputting the second picked-up image to be predicted;
pre-increasing the second picked-up image for N patterns to obtain N of the second picked-up images;
subjecting each of the N of the second picked-up images to geometric transformation for 8 patterns involving a combination of 90×L degree rotation and inversion or non-inversion;
individually inputting 8×N of the second picked-up images having undergone geometric transformation to an identifier that has performed machine learning based on the reference image to obtain 8×N of inference values; and
averaging 8×N of the inference values to obtain an eventual inference value, wherein N is an integer that is equal to or greater than 2 and L is an integer from 0 to 3, inclusive.

13. The image processing method according to claim 12, further comprising:
inputting a high-resolution rectangular image as the second picked-up image; and
preparing, beforehand, a low-resolution square image from the high-resolution rectangular image.

* * * * *